United States Patent [19]

Lang

[11] Patent Number: 5,795,340
[45] Date of Patent: Aug. 18, 1998

[54] MICROCATHETER SET

[76] Inventor: Volker Lang, Zugspitzstrasse 52, 82131 Gauting, Germany

[21] Appl. No.: 687,357
[22] PCT Filed: Dec. 23, 1994
[86] PCT No.: PCT/EP95/04298
§ 371 Date: Nov. 6, 1996
§ 102(e) Date: Nov. 6, 1996
[87] PCT Pub. No.: WO95/20987
PCT Pub. Date: Aug. 10, 1995

[30] Foreign Application Priority Data

Feb. 5, 1994 [DE] Germany ............... 44 03 630.2

[51] Int. Cl.$^6$ ...................................... A61M 25/00
[52] U.S. Cl. ............ 604/283; 604/905; 604/32; 604/248; 604/280
[58] Field of Search ............ 604/30, 32, 246, 604/248, 280, 283, 905

[56] References Cited

U.S. PATENT DOCUMENTS

| | | | |
|---|---|---|---|
| 4,588,402 | 5/1986 | Igari et al. | 604/408 |
| 5,104,387 | 4/1992 | Pokorney et al. | 604/248 |
| 5,156,598 | 10/1992 | Skakoon et al. | 604/283 |
| 5,466,228 | 11/1995 | Evans | 604/248 |

FOREIGN PATENT DOCUMENTS

| | | |
|---|---|---|
| 0372277 | 6/1990 | European Pat. Off. . |
| 2395037 | 1/1979 | France . |
| 2452653 | 10/1980 | France . |
| 2522969 | 9/1983 | France . |
| WO 91/18632 | 12/1991 | WIPO . |

*Primary Examiner*—Michael Powell Buiz
*Assistant Examiner*—Jennifer R. Sadula
*Attorney, Agent, or Firm*—Dilworth & Barrese

[57] ABSTRACT

The invention relates to a microcatheter set with a minimized dead space which has a medicine application and flushing device especially suitable for intensive paediatric-neonatologial medicine. It makes it possible not only to apply infusion therapy via a microcatheter inserted into a large body vein but also to administer drugs repeatedly without any danger via the medicine application and flushing device integrated within the set, even with highly pharmacologically effective additives to the general infusion solution, and/or to do away with partial and total catheter shut-offs. This thus excludes additional stress on and risk for the patient by the repeated application of peripheral infusions or the use of surgically inserted double-lumen central catheters for the intravenous administration of drugs.

21 Claims, 2 Drawing Sheets

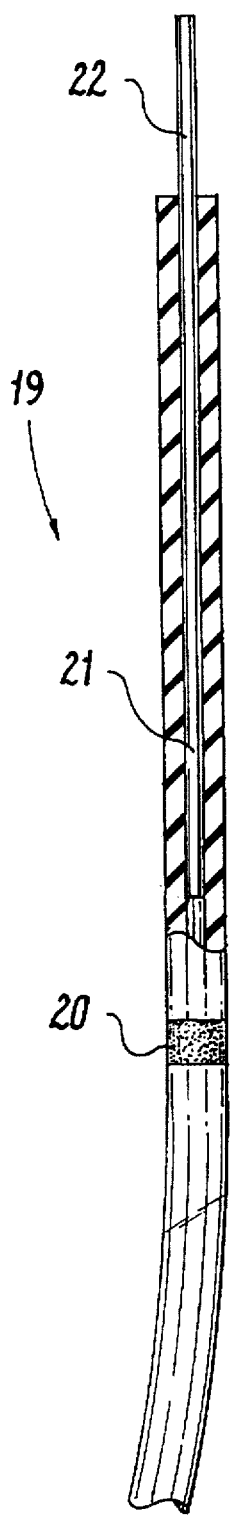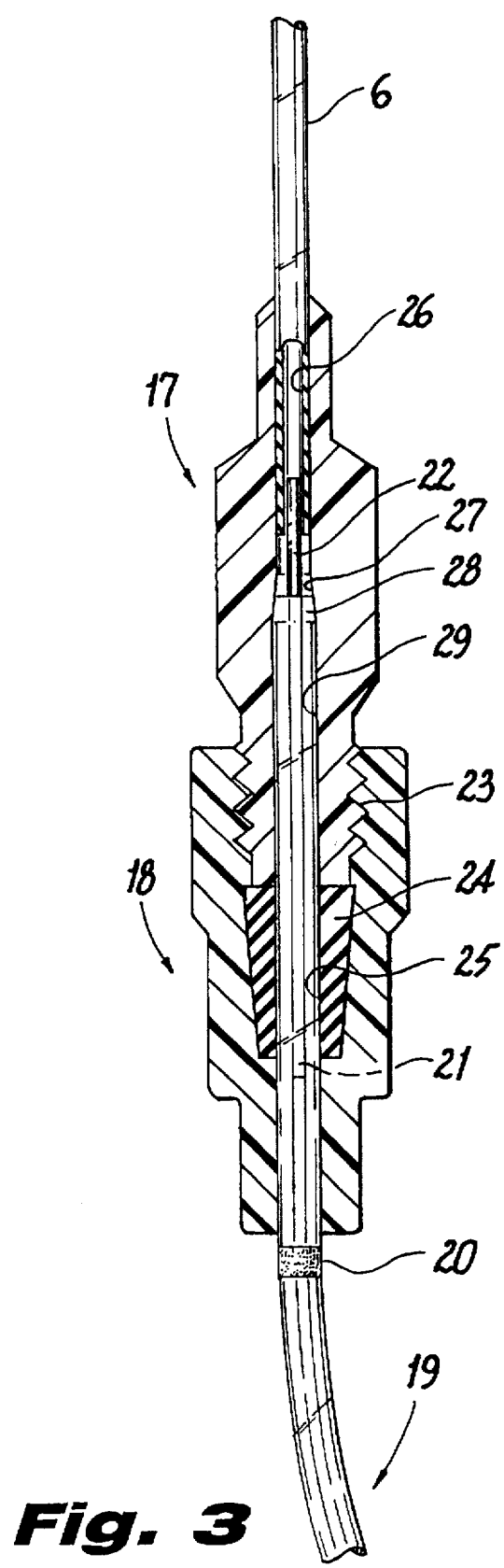

MICROCATHETER SET

BACKGROUND OF THE INVENTION

The invention refers to a microcatheter set in particular an epicutaneo cava microcatheter set, consisting of a microcatheter, an easy-lock catheter connection device with a hose and a standard Luer lock connector.

Above all in the field of neonatology, for the treatment of very undeveloped premature babies who cannot yet be fed orally with milk, it is necessary for modern intensive medical care that there exists the possibility of parenteral alimentation with high-percentage nutrient-rich infusion solutions which, however, can only be applied centrally by means of catheters through venous blood vessels of a wide lumen. A catheter technique which has proved a success in particular in the field of neonatology is the one according to Shaw which uses epicutaneo cava microcatheters. Respective catheters are available on the market in a set. Here the different infusion solutions are usually infused by means of accurately metering injection pumps via distributors and adapters through the connected microcatheter into a large central body vein.

However, in this connection, the following unsolved clinical/pharmacological problems occur: The microcatheter set consisting of a Luer lock adapter, connecting hose, easy lock catheter connection, and a microcatheter, has, as a whole, a dead space volume which is too large. And, in particular when highly effective pharmacological preparations with cardiovascular action (e.g. catecholamine) are added to the infusion fluid —which happens quite often in practice —this means, however, that when, for example, a partially or completely obstructed catheter is flushed or when drugs are administered, that the said large dead space fluid volume with pharmacological preparations influencing the circulatory system will get into the blood stream as a bolus within a very short time. Possible results thereof are severe circulation sensations which, in the case of small premature babies, are possibly followed by life-threatening cerebral hemorrhages. Thus, due to the aforesaid reasons, in the case of partial or complete obstructions, the microcatheters may only be flushed if infusion solutions are used which, pharmacologically, are as indifferent as possible. The same also applies to the administration of medicine. This means in practice, however, that a second access to a vein of the patient has to be created which means discomfort for the patient and the attending physician, in particular in the case of small premature babies and new-born babies. The same is also true for another alternative, namely the use of central double-lumen vein catheters.

SUMMARY OF THE INVENTION

The object of the present invention is to further develop a microcatheter set according to in particular an epicutaneo cava microcatheter, an easy-lock catheter connection device with a hose and a standard Luer lock connector such that the above-cited clinical problems can be solved.

Said object is solved by means of a microcatheter set of the generic type which shows the characterizing features of Luer lock connectors with a minimized dead space, micro-lumen hoses and an easy-lock catheter connection with a minimized dead space being used for the general reduction of the dead space of the microcatheter set, and adjacent to the patient and the catheter and closely to and in front of the easy-lock catheter connection with a small dead space, a flushing and medicine application device being additionally arranged.

Further advantageous aspects of the inventive solution result from the description herein.

BRIEF DESCRIPTION OF THE DRAWINGS

Further details and advantages of the invention will be explained in detail by means of an embodiment illustrated in the drawings, wherein FIG. 2 is a longitudinal section through a microcatheter with inserted tubule, and FIG. 3 an embodiment of an easy-lock catheter connection device according to the invention.

DESCRIPTION OF THE PREFERRED EMBODIMENTS

Figure 1:
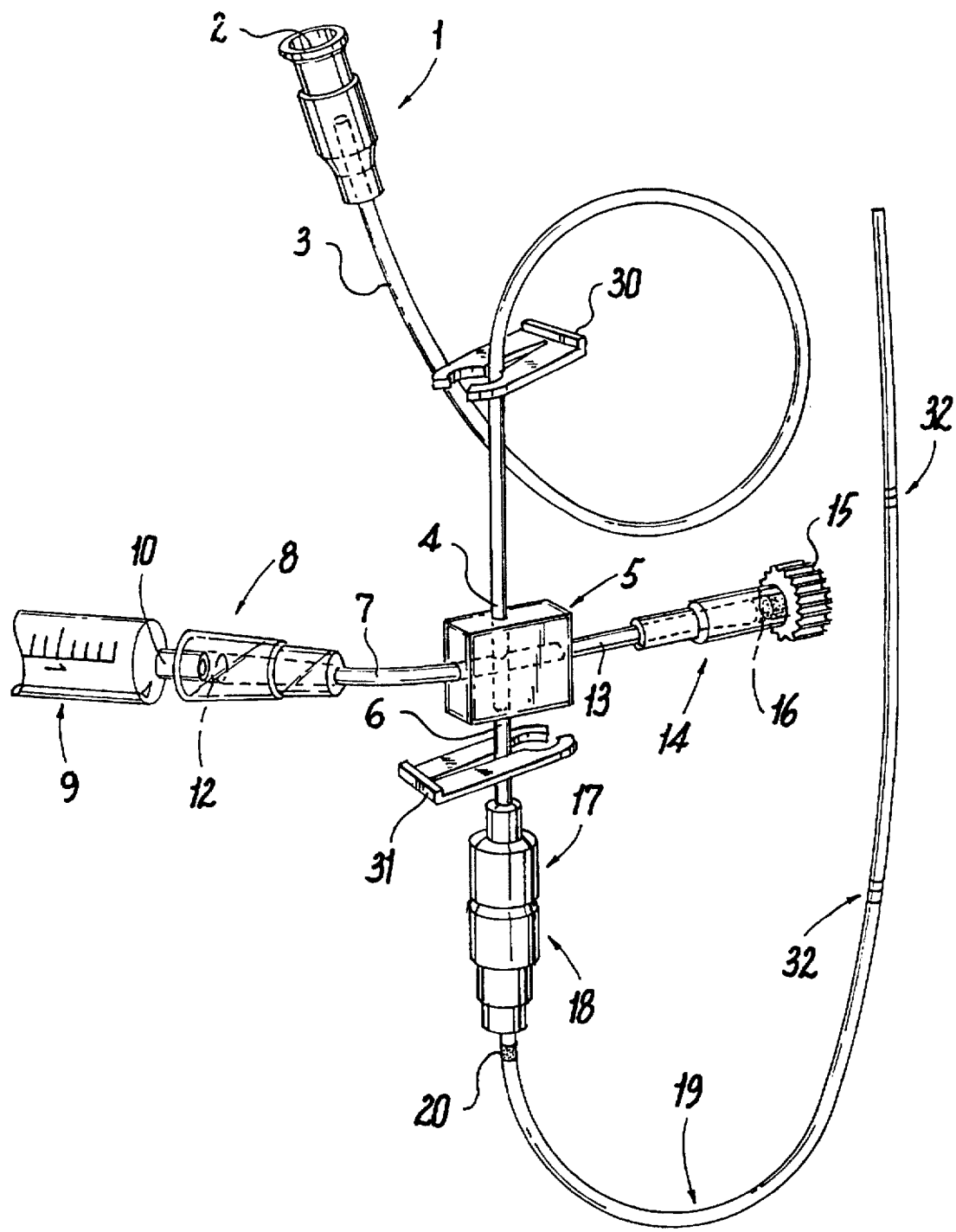
FIG. 1 is a perspective view of a microcatheter set according to the invention.

FIG. 1 shows in a perspective view the disposable sterile epicutaneo cava microcatheter set with a minimized dead space in an assembled state. It consists of a female standard Luer lock adapter 1 designed so that it has a small dead space and made of transparent plastics material, which has a tapering cylindrical cavity 2 for receiving the cone of a male standard Luer lock connector. Said cavity 2 has only such a depth that commercially available male Luer lock cones of slightly varying lengths can only just be locked in a safe and fluid-tight manner. Thereby the dead space forming between the cone end and the bottom of the cylindrical cavity 2 can be reduced to a minimum of 25 to 50 µl. From said bottom of the cylindrical cavity a small-lumen and thick-walled but, nevertheless, flexible transparent plastics hose 3 (inner diameter: 0.5 mm ; length: 100 through 200 mm) leads to a cuboid quadruple connecting piece 5 of transparent synthetic resin. Within the quadruple connecting piece 5 there are provided bores crossing each other at right angles. At one end of two opposing ends thereof the end 4 of hose 3 is inserted, and at the other end thereof a narrow-lumen short connecting hose piece 6 is inserted which belongs to the easy lock connection which is formed by screwing-together two parts 17, 18 and is associated with microcatheter 19. With one side of the horizontally extending bore of the quadruple connecting piece, a small narrow-lumen connecting hose 7 is connected at which a female Luer lock connector 8 with small dead space is attached, upon which a disposable syringe 9 is placed, and on the other side thereof a corresponding connecting hose 13 with connector 14 is attached.

From FIG. 1 it can be inferred that the male Luer lock cones 10 of the disposable syringe 9 or of the Luer lock plug 15 locked by rotating it, which are inserted into the female Luer lock connectors 8 or 14 having a small dead space, do not completely fill these up and therefore allow the creation of a dead space 12 or 16 of slightly differing size, in which the connecting hoses 7 or 13 end up.

FIG. 2 is a longitudinal section through a microcatheter 19 having a ring marking 20 and longitudinal markings 32. The microcatheter 19 can b e made of a soft silicone rubber or polyurethane with radiographic properties. The microcatheter 19 is slipped under pressure over a tubule made of stainless steel 21, wherein the front fifth part 22 of the tubule with respect to the total length is left free. Said front part is used for pushing it into the easy lock connector 17, 18.

FIG. 3 shows a longitudinal section through the easy lock catheter connection in the mounted state. Connecting hose 6 is inserted into part 17 of the easy lock connector. In its narrow lumen 26 there is located the front part 22 of the stainless steel tubule 21. At its lower end, part 17 of the easy lock connection has a threaded connecting piece 23 which, centrally, has a wide guiding channel 29 for the microcatheter 19 slipped over the stainless steel tubule, which continues in an insertion funnel 27 which finally terminates in the lumen of the connecting hose 6. As the microcatheter 19 is pressed into said insertion funnel 27 during the screwing-together of the connector 17, 18, it forms a sealing bead 28 therein. The lower part 18 of the easy lock connector represents a tapped bush made of synthetic resin which tapers in the downward direction and receives a conical rubber plug 24 with a central bore 25 in said part. Into said central bore 25, the microcatheter is inserted with its part 21 to such a degree that its ring marking 20 is still visible at the edge of the lower opening of part 18.

The function of the microcatheter set in operation can be described by means of FIGS. 1 through 3 as follows. The sterile microcatheter set with integrated flushing and medicine application device is connected with its female Luer lock connector 1 with reduced dead space to a syringe pump infusion system with a male Luer lock connecter (not shown). As already described, after the locking of female and male connectors a remaining dead space volume is always created which depends on the accuracy of fit of the male connector cone and amounts to approximately 25 through 50 µl. The attached narrow-lumen connecting hose 3 (with an inner diameter of 0.5 mm) adds further 38 µl, the quadruple connecting piece 5 adds further 7 µl, the connecting hose 6 adds further 4 µl, and, finally, the easy lock connector 17, 18 with its minimized dead space adds further 5 µl. The result is a total dead space volume of approximately 54 µl. In this case, depending on the length and the inner diameter of the microcatheter, a further dead space volume must be added thereto which is caused by said microcatheter. When the used microcatheter has, for example, a length of 150 mm, then 10.5 µl of volume must be added. When, for instance, a partially obstructed microcatheter is flushed free, within a very short time a total of approximately 90 through 120 µl of infusion liquid with possibly added highly effective pharmacological preparations from the dead space volume will be supplied to the patient, which can result in life-threatening overdoses. In comparison thereto, in the microcatheter sets available today in which all the mentioned special measures for reducing the dead space volume are not implemented, at least 240 µl of dead space volume has to be expected.

In order to avoid said mentioned large dead space volumes which, from the clinical aspect, substantially do not only forbid a flushing of the catheter set, but also any drug application, the quadruple connecting piece 5 has been inserted in the microcatheter set according to the invention adjacent to the patient and the catheter for flushing and medicine application, as can be seen in FIG. 1. If the microcatheter 19 is, for instance, to be flushed free or, which is also very often desired, is used for the administration of drugs, this can be performed in the following manner without any risk to the patient (see FIG. 1).

From the female Luer lock connector 8 the Luer lock plug (not shown) is removed and, instead thereof, e.g. a disposable 2 ml syringe 9 filled with physiological saline solution is placed thereupon. Now two sliding hose clamps 30, 31 provided at the hoses 3 and 6 are closed and the Luer lock plug 15, which is closed by turning it, is loosened, and, thus, the Luer connector 14 is opened. First the dead space 12 is filled with the infusion liquid, i.e. approximately 25 through 50 µl, then the connecting hose 7, i.e. approximately 7 µl, a part of the horizontal bore in the distributor 5, i.e. approximately 7 µl, the connecting hose 13, i.e. approximately 7 µl, and the dead space 16 of the Luer connector 14, i.e. 25 through 50 µl. That means finally approximately 75 through 175 µl dead space volume liquid, are flushed by means of the syringe 9 with the physiological saline solution.

When now the Luer lock plug is again locked and the sliding hose clamp 31 is opened, then the flushing or the desired medicine administration can be carried out slowly and continuously via the microcatheter 19 through the Luer connector 8 in one or several minutes, at best by means of an infusion syringe pump now connected therewith. In this case, the dead space volume filled with infusion solution of now 19 µl results from the dead space volume of the used microcatheter with a length of 150 mm with 10.5 µl, of the easy lock connector with 5 µl and of the connecting hose 6 with 3.5 µl (see FIG. 1).

When, for instance, an infusion rate of 1 ml per hour is set for the first one or two minutes after the start of the infusion at the infusion syringe pump connected with the connector 8, then, in practice, catheter medicine applications and flushings can be carried out even where the smallest premature babies are concerned without any risk to the patient. Here, now only 19 µl of infusion solution will be administered into the vascular system of the patient even in a protracted manner within said period.

If the general infusion therapy is to be continued after the administering of medicine or after flushing, then the drug infusion pump can be disconnected from the Luer lock connector 8 which then can be closed by a Luer lock plug which corresponds to plug 15. Subsequently thereto, the sliding hose clamp 30 is opened and thereby the infusion flow via the Luer lock adapter 1 and the connecting hose 3 is again set free.

What is claimed is:

1. In a microcatheter set, in particular an epicutaneo cava microcatheter set, comprising a microcatheter (19), a catheter connection device (17,18) for connecting the microcatheter (19) with one end of a first hose (6,3) and a first standard Luer lock connector (1) coupled to an opposite end of the first hose (6,3), wherein an integrated flushing and medicine application device (9) is arranged in communication with the first hose (3,6) through a second micro-lumen hose (7) and second Luer lock connector (8) and close to and in front of the catheter connection device (17,18), and the second Luer lock connector (8), first hose (6.3) which is a micro-lumen hose, second micro lumen hose (7) and catheter connection device (17,18) are each formed and arranged with respect to one another to provide minimized dead space, resulting in reduction of overall dead space in the microcatheter set.

2. Microcatheter set according to claim 1, additionally comprising a quadruple distributor or four-way cock (5) arranged to couple the integrated flushing and medicine application device (6) with said first hose (3,6).

3. Microcatheter set according to claim 2, wherein said quadruple distributor (5) comprises two channels running therethrough and crossing one another at substantially right angles.

4. Microcatheter set according to claim 3, wherein said quadruple distributor (5) is made of plastic and provided with a substantially cuboid shape.

5. Microcatheter set according to claim 3, wherein said second micro-lumen hose (7) coupled to said integrated flushing and medicine application device (9) is inserted into one end of one of said two channels, with a third connecting micro-lumen hose (13) being inserted into an opposite end of said one channel at one end thereof and a third female Luer lock connector (14) being coupled to an opposite end of said third connecting hose (13).

6. Microcatheter set according to claim 3, wherein in a first one of said two channels, a micro-lumen supply hose (4) and a micro-lumen output hose (6) forming sections of said first hose (3,6) are respectively inserted at opposite ends thereof in a tightly closing manner.

7. Microcatheter set according to claim 6, additionally comprising a one-way valve coupled in said micro-lumen supply hose (4) and arranged to permit direction of fluid flow towards a patient, said valve being biased or unbiased.

8. Microcatheter set according to claim 6, wherein in a second one of said two channels, short micro-lumen connecting hoses (7,13) are inserted at opposite ends thereof in a tightly closing manner, one of said short connecting hoses being said second micro-lumen hose (7), and female Luer lock connectors (8,14) with minimized dead space and arranged to be closable by rotation of a respective Luer lock plug (15) are carried at opposite ends of said short hoses (7,13), with one (8) of said Luer lock connectors (8,14) being said second Luer lock connector (8).

9. Microcatheter set according to claim 1, wherein said connection device (17,18) comprises a female part (18) possessing a tapering cylindrical cavity (18) and a resilient disk or plug (24) possessing a central recess (25) and arranged such that dead space therein is completely filled up by said resilient disk or plug (24).

10. Microcatheter set according to claim 1, wherein said connection device (17,18) comprises a male part (17) formed with a conical shape at a front protruding end thereof, and a resilient disk or plug (24) provided with a central recess (25) and arranged upon the conical front of said male connector (17) when connection is carried out, such that dead space of the male connector (17) is completely filled up by said resilient disk or plug (24).

11. Microcatheter set according to claim 1, additionally comprising a Luer lock plug (17) having an elongated thread (25) as a male member (17) of said connection device (17,18) with said plug (17) arranged to be locked in said device (17,18) by rotation through one or two turns.

12. Microcatheter set according to claim 1, additionally comprising a stainless steel tubule (21) over which the microcatheter (19) is positioned under pressure such that a front part (22) of the tubule (21) remains uncovered.

13. Microcatheter set according to claim 12, wherein said connection device (17,18) comprises a guiding channel (29) formed with an insertion funnel (27) situated therein which, upon insertion of the uncovered part (22) of said tubule (21) thereinto, converts the pressed-in catheter (19) which is elastic, into a sealing bead (28).

14. Microcatheter set according to claim 12, wherein a tip of the uncovered front end (22) of said tubule (21) is sealingly pressed into a narrow lumen of the attached first connecting hose (6) after coupling parts (17,18) of said connection device (17,18) are screwed together.

15. Microcatheter set according to claim 1, wherein said female Luer lock connector (1) comprises a tapering cylindrical cavity (2) for receiving a cone of a male standard Luer lock connector, such that dead space formed between an end of the cone and a bottom of the cylindrical cavity (2) is reduced to a minimum of about 25 to 50 microliters, and male (17) and female (18) parts of said connection device (17,18) are formed such that, after locking of the same together, a remaining dead space volume created within said connection device (17) amounts to approximately 25 to 50 microliters.

16. A microcatheter set structured and arranged for feeding of premature infants therethrough, comprising a microcatheter (19), a catheter connection device (17,18) comprising male (17) and female (18) parts arranged to be screwed together in order to couple the same, with one of said parts (17,18) being coupled to an end of said microcatheter (19), a plurality of first connecting hoses (3,4,6) arranged to be coupled, at one end thereof, to said catheter connection device (17,18), a first female Luer lock adapter (1) arranged to be coupled to an opposite end of said plurality of first connecting hoses (3,6), a quadruple distributor (5) comprising two channels running therethrough at substantially right angles to one another, with said plurality of hoses coupled to opposite ends of a first one of said channels, a plurality of second connecting hoses (7,13) respectively coupled with opposite ends of a second one of said channels, a plurality of additional female Luer lock connectors (8,14) each arranged to be respectively coupled to opposite ends of said plurality of second connecting hoses (7,13), an integrated flushing and medicine application device (9) arranged in communication with one of said additional female Luer lock connectors (8,14), and a Luer lock plug (15) arranged to be inserted into the other one of said additional female Luer lock connectors (8,14) by rotation, wherein all said female Luer lock connectors (1,8,14), said catheter connection device (17,18) and all said hoses (4,6,7,13) which are micro-lumen hoses, are each formed with minimized dead space, resulting in reduction of overall dead space upon assembly of the microcatheter set.

17. Microcatheter set according to claim 16, wherein said catheter connection device (17,18) comprises:

a female part (18) possessing a tapering cylindrical cavity (18), a male connector (17) formed with a conical projection at a front end thereof and provided with threads (23) thereabout, by means of which the male (17) and female (18) parts can be locked together by rotation, and a resilient plug (24) possessing a central recess (25) extending therethrough and arranged either on the conical projection of the male member (17) or in a bottom of the tapering cylindrical cavity (18) of the female part (18) such that any dead space within said connector parts (17,18) is completely filled up by said resilient plug (24) when said parts (17,18) are screwed together.

18. Microcatheter set according to claim 17, additionally comprising, a stainless steel tubule (21) arranged to be inserted into an end of said microcatheter (19) which is elastic, such that a front part (22) of said tubule (21) protrudes from said microcatheter (19), and said connection device (17,18) comprises a guiding channel (29) formed with an insertion funnel portion (27) such that when said elastic catheter (19) with said tubule (21) inserted through an end thereof is coupled into the connection device (17,18) which is secured together, the pressed-on elastic catheter (19) is converted into a sealing bead (28).

19. A method for flushing a microcatheter according to claim 16, comprising the steps of removing any Luer lock plugs (15) from one of said additional female Luer lock connectors (8) and inserting, thereinto, a disposable syringe (9) filled with flushing solution, clamping (30,31) said first connecting hoses (3,6), loosening Luer lock plug (15) secured in the opposite additional female Luer lock connector (14) by turning, such that said opposite additional female Luer lock connector (14) is opened, filling dead space (12) within said first additional female Luer lock connector (8) with infusion liquid, removing the syringe (9) and re-locking the previously-opened female Luer lock connectors (8,14) which are now filled with infusion liquid, unclamping (31) the hose (6) coupled to the microcatheter (19) through said connecting device (17,18), and carrying out flushing or desired medicinal administration slowly and continuously via said microcatheter (19) through said first additional Luer lock connector (8).

20. Connection device for a microcatheter, comprising male and female parts (17,18) having respective channels extending therethrough for coupling of the microcatheter (19) to a connecting hose (6) at opposite ends thereof, said male (17) and female (18) members possessing complementary threads such that said members (17,18) can be screwed together to couple the same, said female member (18) comprising a tapering cylindrical cavity (18), said male member (17) comprising a conical projection at a front end thereof, and additionally comprising a resilient disk or plug (24) possessing a central recess (25) extending therethrough, and arranged such that when said disk or plug (24) is seated either upon said conical projection or within said tapering cylindrical cavity (18) and said male and female (17,18) members are screwed together, dead space within said connection device (17,18) is completely filled up by said resilient disk or plug (24).

21. The device of claim 20, additionally comprising a glass or stainless steel tubule (21) arranged to be inserted into an end of said microcatheter (19) such that an end (22) of said tubule (21) protrudes from said microcatheter (19) which is elastic, and said coupling device (17,18), is arranged such that a guiding channel (29) extending therethrough comprises a funnel shaped portion (27) positioned such that, when said catheter (19) with said protruding tubule (21) is inserted into said connection device (17,18) which is then screwed together, an end or portion of said pressed-in elastic catheter (19) is converted into a sealing bead (28).

* * * * *